United States Patent
Anderson

(12) 
(10) Patent No.: US 6,558,666 B1
(45) Date of Patent: May 6, 2003

(54) CHROMIUM-CONTAINING CARBOHYDRASE ENZYME FOOD SUPPLEMENT COMPOSITION

(75) Inventor: Mark L. Anderson, Chester, NY (US)

(73) Assignee: Triarco Industries, Inc., Wayne, NJ (US)

( * ) Notice: Subject to any disclaimer, the term of this patent is extended or adjusted under 35 U.S.C. 154(b) by 0 days.

(21) Appl. No.: 10/114,042

(22) Filed: Apr. 3, 2002

(51) Int. Cl.$^7$ .................. A61K 38/54; A61K 31/555
(52) U.S. Cl. ........................... 424/94.2; 514/188
(58) Field of Search ................ 424/94.2; 514/188

(56) References Cited

U.S. PATENT DOCUMENTS

| | | | |
|---|---|---|---|
| 4,292,331 A | 9/1981 | Ostre | 426/52 |
| 5,057,321 A | 10/1991 | Edgren et al. | 424/413 |
| 5,817,350 A | 10/1998 | Rhode, Jr. et al. | 426/2 |

FOREIGN PATENT DOCUMENTS

GB   1107824   3/1968

OTHER PUBLICATIONS

International Journal of Sport Nutrition, 1991, 1, 289–293 "Nutritional Ergogenic Aids: Chromium, Exercise and Muscle Mass" Priscilla M. Clarkson.

Human & Experimental Toxicology (2001) 20, 439–451, "Mechanisms of chromium toxicity, carcinogenicity and allergenicity: Review of the literature from 1985 to 2000" AD Dayan and AJ Paine.

Nutrition Reviews, vol. 56, No. 9 Sep. 1998; 266–270, "Effects of Chromium on Body Composition and Weight Loss" Richard A. Anderson, Ph.D., C.N.S.

International Journal of Sport Nutrition, 1992, 2, 111–122, "Efficacy of Chromium Supplementation in Athletes: Emphasis on Anabolism" Robert G. Lefavi, Richard A. Anderson, Robert E. Keith, G. Dennis Wilson, James L. McMillan, and Michael H. Stone.

International Journal of Sport Nutrition, 2000, 10, 476–485, "Effects of Carbohydrate and Chromium Ingestion During Intermittent High–Intensity Exercise to Fatigue" J.Mark Davis, Ralph S. Welsh, and Nathan A. Alderson.

*Primary Examiner*—Raymond Henley, III
(74) *Attorney, Agent, or Firm*—Fitzpatrick, Cella, Harper & Scinto

(57) ABSTRACT

A chromium(III)-containing carbohydrase enzyme food supplement composition providing at least one cellulase fungal enzyme, at least one alpha amylase fungal enzyme, at least one hemicellulase fungal enzyme, at least on chromium (III) compound, and, optionally, at least one acceptable carrier.

20 Claims, No Drawings

CHROMIUM-CONTAINING CARBOHYDRASE ENZYME FOOD SUPPLEMENT COMPOSITION

BACKGROUND OF THE INVENTION

1. Field of the Invention

The present invention relates generally to endurance improving carbohydrase enzyme food supplements. In particular, the invention relates to an endurance improving carbohydrase enzyme food supplements comprising a unique combination of at least one cellulase fungal enzyme, at least one alpha amylase fungal enzyme, at least one hemicellulase fungal enzyme, and at least one chromium (III) compound.

2. Related Prior Art

Many athletes rely upon various carbohydrate-containing foods and carbohydrate-containing food supplements in order to provide an ample supply of nutrients for energy production. Many popular food supplements used by athletes today are based on glucose polymers rather than starch. The glucose polymers used in such supplements are typically known collectively as maltodextrins and oligosaccharides, and are considered more desirable because they yield their energy more slowly than does simple sugar or starch. This provides a smoother rise in blood glucose that, in turn, results in a slower and more sustained energy boost.

U.S. Pat. No. 5,817,350 to Rhode, Jr., et al. discloses carbohydrase fungal enzyme food supplement compositions intended to replace food supplements containing glucose polymers by using the human stomach as a reaction vessel in which ingested insoluble dietary starches and other complex carbohydrates are converted into soluble dextrins and oligosaccharides, which are then used by the body as a primary source of energy over a prolonged period of time. When taken in the form of a tablet, capsule, powder, or liquid food supplement with carbohydrate-containing foods or carbohydrate-containing food supplements, the carbohydrase fungal enzyme food supplement compositions convert ingested insoluble dietary starches and other complex carbohydrates into soluble dextrins and oligosaccharides, which can then be used by the body as a primary source of energy.

The carbohydrase fungal enzyme food supplement compositions disclosed in U.S. Pat. No. 5,817,350 are of value to athletes, such as, e.g., joggers, cyclers, distance runners, and other endurance athletes, seeking to prolong the blood glucose elevation that follows ingestion of assimilable carbohydrates in that the carbohydrase fungal enzyme food supplement compositions hydrolyze starches and other carbohydrates in the stomach to produce glucose polymers, thereby freeing the athlete from reliance upon expensive and inconvenient supplements. The combination of carbohydrase fungal enzymes effectively converts insoluble dietary starches in the gastrointestinal tract into soluble energy-rich maltodextrins and oligosaccharides, which mediates the release of glucose from starches in a sustained release manner.

Chromium(III) is known to be an essential trace mineral, such that small quantities must be ingested on a regular basis to maintain the health of an individual. For example, Clarkson et al., *International Journal of Sport Nutrition*, 1991, 1, 289–293, report that the National Research Council has established a recommended dietary allowance ("RDA") of from 50 to 200 µg of chromium as a safe and adequate daily dietary intake, and that chromium serves as a cofactor to insulin action. Clarkson et al. studied the effect of chromium supplementation of 200 µg daily on lean body mass, and found that male college athletes participating in weight-lifting programs taking a chromium supplement showed a significant increase in lean-body mass when compared to others in the program taking a placebo. However, Clarkson et al. recommend taking a chromium supplement only when chromium intake is suboptimal.

Anderson, *Nutrition Reviews*, 1998, 56, 266–270, reports that human studies on the effects of chromium on lean body mass failed to show an effect of a 200 µg chromium supplement on body composition, but that positive results were obtained after 24 weeks when a 400 µg chromium supplement was taken.

Lefavi et al., *International Journal of Sport Nutrition*, 1992, 2, 111–122, report that athletes may have an increased requirement for chromium due to excessive chromium loss and marginal chromium intake resulting from exercise. Lefavi et al. also report that, as chromium is a nutrient and not a drug, anabolic steroid-like muscle mass increases following dietary supplementation of any chromium compound in normal, healthy athletes should not be expected.

Davis et al., *International Journal of Sport Nutrition and Metabolism*, 2000, 10, 476–485, report that acute chromium supplementation prior to exercise does not improve performance and resistance to fatigue. Test results indicate that ingestion of a carbohydrate electrolyte drink prior to and during exercise did provide a benefit, but the addition of chromium did not enhance the effect provided by the carbohydrate-electrolyte drink.

It has been unexpectedly found that the addition of at least one chromium(III) compound to a carbohydrase fungal enzyme food supplement composition, such as those disclosed in U.S. Pat. No. 5,817,350 to Rhode, Jr., et al., the contents of which are incorporated herein in their entirety by reference, enhances endurance and fatigue resistance when compared to other endurance enhancing food supplements, including the compositions disclosed by Rhode, Jr. et al.

SUMMARY OF THE INVENTION

The present invention is directed to a chromium(III)-containing enzyme food supplement composition comprising effective amounts of at least one cellulase fungal enzyme, at least one alpha amylase fungal enzyme, at least one hemicellulase fungal enzyme, at least one chromium (III) compound, and, optionally, at least one acceptable carrier. Preferably, the cellulase fungal enzyme is present in an amount of at least 1,000 CA per gram of composition, the alpha amylase fungal enzyme is present in an amount of at least 1,000 DU per gram of composition, and the hemicellulase fungal enzyme is present in an amount of at least 50 HCU per gram of composition. The chromium(III) compound is preferably present in an amount equivalent to up to about 475 µg of elemental chromium, more preferably in an amount of from about 50 µg to about 400 µg of elemental chromium, most preferably an amount of from about 200 µg to about 400 µg of elemental chromium, and may be an ionic chromium(III) compound or a chelated chromium(III), such as, e.g., an amino acid chelate of chromium(III), an organically bound chromium(III), chromium nicotinate, chromium polynicotinate, or chromium picolinate.

The invention is further directed to a method of improving endurance and fatigue resistance in a mammal, including humans. The method comprises administering a chromium (III)-containing enzyme food supplement composition of the invention to a mammal prior to or during exercise by the mammal, thereby improving endurance and fatigue resistance.

DETAILED DESCRIPTION OF THE INVENTION

As used herein, a Cellulase Activity Unit (CA unit) is defined as that quantity of enzyme required, under the conditions of the assay stated in the Food Chemicals Codex, Third Edition, General Tests and Apparatus, Cellulase Activity, pp 483–484, to reduce the viscosity of 200 grams of a 5% solution of the specified sodium carboxymethylcellulose substrate from 400 to 300 cps at 35° C. and pH 5.0 in one hour. An Alpha-Amylase Dextrinizing Unit (DU unit) is defined as the quantity of alpha-amylase that will, under the conditions of the assay stated in the above-referenced text, section Alpha Amylase Activity (Non-Bacterial), pp 479–482, dextrinize soluble starch in the presence of an excess of beta-amylase at the rate of one gram per hour at 30° C. A Hemicellulase Unit (HCU unit) is defined as that activity that will produce a relative fluidity change of 1 over a period of five minutes in a locust bean gum substrate under the conditions specified in the assay stated in the above-referenced texts, section Hemicellulase Activity, pp 490–491.

Also, as used herein, the term chromium(III) compound includes organic and inorganic chromium (III) compounds and chelates. Such compounds include, but are not limited to purified chromium(III) compounds, extracted chromium(III) compounds, and chromium(III) compounds that are found in matter from non-toxic plants, such as, e.g., mustard or yeast, that have absorbed chromium(III) from water or soil.

The present invention is directed to chromium(III)-containing carbohydrase fungal enzyme food supplement compositions. The chromium(II)-containing carbohydrase fungal enzyme food supplement compositions of the invention comprise at least one chromium(III) compound, at least one cellulase fungal enzyme, at least one alpha amylase fungal enzyme, and at least one hemicellulase fungal enzyme. Preferably, the carbohydrases used are obtained from fungal sources, as it has been found that fungal cellulase, alpha amylase, and hemicellulase carbohydrase enzymes provide optimum results.

Preferably, the chromium(III) compound is an ionic chromium(III) compound or a chelated chromium(III), such as, e.g., an amino acid chelate of chromium(III), an organically bound chromium(III), chromium nicotinate, chromium polynicotinate, and chromium picolinate. Chromium(III) may also be provided in an edible part of a plant that was grown with a chromium supplement added to the plant soil or water in an amount sufficient for an uptake of the chromium(III) by the plant.

The cellulase fungal enzymes useful in the invention are preferably enzymes derived from a fungal source that are capable of degrading cellulose. Cellulase fungal enzymes useful in the invention include, but are not limited to those obtained from *Aspergillus niger* or *Trichoderma reesei*, which is also referred to as *Trichoderma viride*.

Useful hemicellulase fungal enzymes are preferably enzymes derived from a fungal source capable of hydrolyzing specific types of hexosans and pentosans, including, but not limited to, more or less complex mannans, galactans, and xylans. Hemicellulase fungal enzymes useful in the invention include, but are not limited to, those obtained from *Aspergillus niger*.

Useful alpha amylase fungal enzymes are preferably derived from a fungal source capable of breaking down starch into dextrins by hydrolysis. Alpha amylase fungal enzymes useful in the invention include those obtained from *Aspergillus oryzae, Aspergillus niger* and *Rhizopus oryzae.*

Enzymes useful in the invention may be obtained by culturing the organism, and then extracting and purifying the enzyme by conventional techniques known in the art, but are also available commercially. For example, cellulase and hemicellulase fungal enzymes may be obtained from Bio-Cat, Inc., Industrial Drive, Troy, Va. 22974, and Amano International Enzyme Company, Inc., 250 East Zion Crossroads, Troy, Va. 22974. Fungal amylase enzymes are also available from Bio-cat, Inc. Troy, Va.

The cellulase fungal enzyme, alpha amylase fungal enzyme, and hemicellulase fungal enzyme are preferably used, in accordance with the subject invention, in the following amounts: for the cellulase fungal enzyme, in an amount of at least about 1,000 CA; for the alpha amylase fungal enzyme, in an amount of at least about 1,000 DU; and for the hemicellulase fungal enzyme, in an amount of at least about 50 HCU. As long as the minimum amount is ingested, the amount of enzyme is not critical. However, for reasons of economics, an excessive quantity of enzyme should be avoided, and for reasons of utility, at least the minimum amount to produce satisfactory results should be used.

The chromium(III) compound is preferably present in the chromium (III)-containing carbohydrase fungal enzyme food supplement compositions of the invention in an amount equivalent to up to about 475 $\mu$g of elemental chromium, more preferably in an amount equivalent to from about 50 $\mu$g to about 400 $\mu$g elemental chromium, and most preferably in an amount equivalent to from about 200 $\mu$g to about 400 $\mu$g elemental chromium. Chromium nicotinate, a chromium(III) compound useful in the invention, is also available commercially from InterHealth Nutraceuticals, Benicia, Calif. 94510.

Optionally, the enzyme food supplement compositions of the invention include a carrier material, such as, e.g., maltodextrins, modified starches, direct compression tablet excipients such as dicalcium phosphate, calcium sulfate, and sucrose. A particularly preferred carrier ingredient is the 10 DE Maltrin M100 maltodextrin from Grain Processing Corporation. Preferably, carriers are added in concentrations up to about 95 weight percent, and, more preferably, from about 50 to about 95 weight percent of the total composition. Various other additives which are conventionally added to enzyme food supplement compositions, such as preservatives and the like, may also be utilized.

Chromium(III)-containing carbohydrase fungal enzyme food supplement compositions of the invention may be formulated by dry-blending the enzymes and at least one chromium(III) compound, preferably with a carrier, such as, e.g., maltodextrin, until a uniform mixture is obtained. A preferred chromium (III)-containing carbohydrase fungal enzyme food supplement composition comprises (1) 2.500 weight percent of cellulase, preferably from *Aspergillus niger,* containing 90,000 CA per gram of cellulase enzyme, (2) 2.0835 weight percent of alpha amylase, preferably from Aspergillus oryzae, containing 100,000 DU per gram of alpha amylase enzyme, (3) 0.5000 weight percent of hemicellulase, preferably from *Aspergillus niger,* containing 32,000 HCU per gram of hemicellulase enzyme, (4) an amount of chromium nicotinate equivalent to from about 50 $\mu$g to about 400 $\mu$g of elemental chromium, and (5) and a balance of maltodextrin, where all weight percents are based on the total composition.

The present enzyme food supplement composition is ingested in the same manner as any food product, and, preferably, taken immediately after or during ingestion of the dietary carbohydrates.

The efficacy of the chromium(III)-containing carbohydrase fungal enzyme food supplement compositions of the invention is demonstrated by the examples set forth below, which are presented for illustration purposes only, and are not to be construed as limiting the invention, the scope of which is defined by the appended claims.

EXAMPLES

The differences in the effects of chromium(III), a carbohydrase enzyme composition, and a chromium(III)-containing carbohydrase composition on endurance and resistance to fatigue, as well as blood glucose levels, were tested using the swim times of 30 male Sprague Dawley rats, which had been quarantined for at least one week, fasted for 24 hours before dosing with water ad lib, and acclimated to the swim tank the day before testing.

Test samples were prepared by making a puree of a Met-Rx® food bar, which was used as a carbohydrate energy source. The Carbogen® product, a carbohydrase enzyme composition, comprising 2.500 weight percent cellulase from *Aspergillus niger*, containing 90,000 CA per gram of cellulase enzyme, 2.0835 weight percent alpha amylase from *Aspergillus oryzae*, containing 100,000 DU per gram of alpha amylase enzyme, 0.5000 weight percent hemicellulase from *Aspergillus niger*, containing 32,000 HCU per gram of hemicellulase enzyme, and 94.9165 weight percent maltodextrin, was added to test samples 1, 4,

TABLE 1

| Substrate: Met-Rx Food bar | Average Active Swim Time (min) | Average Time (min) To Exhaustion |
|---|---|---|
| Sample 1 Carbogen ® (1 mg/g carbohydrate) | 10.24 ± 5.53 (±54%) | 12.43 ± 3.19 (±25.7%) |
| Sample 2 Cr Nicotinate (3.1 μg Cr/kg) | 7.82 ± 0.70 (±8.9%) | 9.91 ± 1.85 (±18.7%) |
| Sample 3 Cr Nicotinate (5.76 μg Cr/kg) | 6.53 ± 3.72 (±57%) | 7.81 ± 3.05 (±39%) |
| Sample 4 Carbogen ® (1 mg/g carbohydrate) + Cr (3.1 μg/kg) | 13.64 ± 1.43 (±10.5%) | 16.2 ± 1.05 (±6.5%) |
| Sample 5 Carbogen ® (1 mg/g carbohydrate) + Cr (5.7 μg/kg) | 7.9 ± 3.68 (±46.6%) | 13.12 ± 4.72 (±36%) |

TABLE 2

| Time (hour) | Sample 1 Carbogen ® 1 mg/g | Sample 2 Cr(III) μg/kg | Sample 3 Cr(III) 5.7 ug/kg | Sample 4 Carbogen ® + 3 μg/kg Cr(III) | Sample 5 Carbogen ® + 5.7 ug/kg Cr(III) |
|---|---|---|---|---|---|
| 0 | 89 ± 4.1 | 91 ± 8.7 | 88 ± 7 | 90 ± 3 | 90 ± 7 |
| 1 | 135 ± 12.7 | 138 ± 6.4 | 136 ± 4 | 139 ± 8.1 | 146 ± 8.9 |
| 2 | 136 ± 3.5 | 128 ± 8 | 138 ± 2.1 | 140 ± 6.1 | 138 ± 9.7 |
| 3 | 105 ± 6.7 | 113 ± 9.1 | 104 ± 13.4 | 106 ± 17.5 | 119 ± 14.6 |
| 4 | 100 ± 9 | 137 ± 10 | 106 ± 17.2 | 133 ± 12.7 | 126 ± 5.6 | and 5 at a concentration of 1 mg per gram of carbohydrate. Chromium(III) nicotinate was added to test samples 2 and 4 at a concentration of 250 μg/kg of body weight, and to test samples 3 and 5 at a concentration of 463 μg/kg of body weight. Therefore, the concentration of elemental chromium (III) was 3.1 μg/kg of body weight in test samples 2 and 4 and 5.76 μg/kg of body weight in test samples 3 and 5.

Each animal was dosed with 1 ml/100 g body weight of one of the test samples. Baseline blood samples were drawn before dosing and hourly following dosing. The swim test was initiated two hours and five minutes after dosing. During the test, the time each animal spent actively swimming and the time to exhaustion were measured. The average swim times and average times to exhaustion for each test samples are set forth in Table 1, and the average glucose levels for each test sample are set forth in Table 2.

The test results show a 30 percent increase in average swim time and average time to exhaustion when a dose equivalent to 3.1 μg/kg of elemental chromium(III) is administered in combination with the Carbogen® carbohydrase enzyme composition, despite substantially no increase in blood glucose over Carbogen® alone. However, the data also indicate that the benefit of chromium(III) may decrease above a certain dosage, as the time to exhaustion is only slightly higher for test sample 5 than for test sample 1.

This invention is not limited by the embodiments disclosed herein and it will be appreciated that numerous modifications and embodiments may be devised by those skilled in the art. Therefore, it is intended that the appended claims cover all such modifications and embodiments that fall within the true spirit and scope of the present invention.

What is claimed is:

1. A chromium(III)-containing enzyme food supplement composition comprising effective amounts of at least one cellulase fungal enzyme, at least one alpha amylase fungal enzyme, at least one hemicellulase fungal enzyme, at least one chromium(III) compound, and, optionally, at least one acceptable carrier.

2. The composition according to claim 1, wherein the chromium(III) is present in an amount equivalent to up to about 475 μg of elemental chromium.

3. The composition according to claim 1, wherein the chromium(III) is present in an amount of from about 50 μg to about 400 μg of elemental chromium.

4. The composition according to claim 1, wherein the chromium(III) is present in an amount of from about 200 μg to about 400 μg of elemental chromium.

5. The composition according to claim 1, wherein the chromium(III) is an ionic chromium(III) compound or a chelated chromium(III).

6. The composition according to claim 1, wherein the at least one chromium compound is selected from the group consisting of an amino acid chelate of chromium(III), an organically bound chromium(III), chromium nicotinate, chromium polynicotinate, and chromium picolinate.

7. The composition according to claim 1 wherein the cellulase fungal enzyme is present in an amount of at least 1,000 CA per gram of composition, the alpha amylase fungal enzyme is present in an amount of at least 1,000 DU per gram of composition, and the hemicellulase fungal enzyme is present in an amount of at least 50 HCU per gram of composition.

8. The composition according to claim 7, wherein the chromium(III) is present in an amount equivalent to up to about 475 µg of elemental chromium.

9. The composition according to claim 7, wherein the chromium(III) is present in an amount of from about 50 µg to about 400 µg of elemental chromium.

10. The composition according to claim 7, wherein the chromium(III) is present in an amount of from about 200 µg to about 400 µg of elemental chromium.

11. A method of improving endurance and fatigue resistance in a mammal, the method comprising:
administering a chromium(III)-containing enzyme food supplement composition, the composition comprising effective amounts of at least one cellulase fungal enzyme, at least one alpha amylase fungal enzyme, at least one hemicellulase fungal enzyme, at least one chromium(III) compound, and, optionally, at least one acceptable carrier, to a mammal prior to or during exercise by the mammal, thereby improving endurance and fatigue resistance.

12. The method according to claim 11, wherein the chromium(III) is present in the food supplement composition in an amount equivalent to up to about 475 µg of elemental chromium.

13. The method according to claim 11, wherein the chromium(III) is present in the food supplement composition in an amount equivalent to from about 50 µg to about 400 µg of elemental chromium.

14. The method according to claim 11, wherein the chromium(III) is present in the food supplement composition in an amount equivalent to from about 200 µg to about 400 µg of elemental chromium.

15. The method according to claim 11, wherein the chromium(III) is an ionic chromium(III) compound or a chelated chromium(III).

16. The method according to claim 11, wherein the at least one chromium(III) compound is selected from the group consisting of an amino acid chelate of chromium(III), an organically bound chromium(III), chromium nicotinate, chromium polynicotinate, chromium picolinate.

17. The method according to claim 11, wherein the cellulase fungal enzyme is present in the food supplement composition in an amount of at least 1,000 CA per gram of composition, the alpha amylase fungal enzyme is present in the food supplement composition in an amount of at least 1,000 DU per gram of composition, and the hemicellulase fungal enzyme is present in the food supplement composition in an amount of at least 50 HCU per gram of composition.

18. The method according to claim 17, wherein the chromium(III) is present in the food supplement composition in an amount equivalent to up to about 475 µg of elemental chromium.

19. The method according to claim 17, wherein the chromium(III) is present in the food supplement composition in an amount equivalent to from about 50 µg to about 400 µg of elemental chromium.

20. The method according to claim 17, wherein the chromium(III) is present in the food supplement composition in an amount equivalent to from about 200 µg to about 400 µg of elemental chromium.

* * * * *